US012576236B2

(12) United States Patent
Gangan et al.

(10) Patent No.: US 12,576,236 B2
(45) Date of Patent: Mar. 17, 2026

(54) WEARABLE WEIGHTED APPARATUS

(71) Applicant: NESTED BEAN, INC., Hudson, MA (US)

(72) Inventors: Manasi Gangan, Hudson, MA (US); Susan Sofia-Mcintire, Ganesvoort, NY (US); Apeksha Katta, Lowell, MA (US)

(73) Assignee: NESTED BEAN INC., Hudson, MA (US)

( * ) Notice: Subject to any disclaimer, the term of this patent is extended or adjusted under 35 U.S.C. 154(b) by 931 days.

(21) Appl. No.: 17/329,805

(22) Filed: May 25, 2021

(65) Prior Publication Data

US 2022/0379072 A1     Dec. 1, 2022

(51) Int. Cl.
*A61M 21/02*     (2006.01)
*A41B 13/06*     (2006.01)
(Continued)

(52) U.S. Cl.
CPC ..... *A61M 21/02* (2013.01); *A61M 2021/0022* (2013.01); *A61M 2209/088* (2013.01); *A61M 2240/00* (2013.01)

(58) Field of Classification Search
CPC .......... A61M 21/02; A61M 2021/0022; A61M 2209/088; A61M 2240/00; A63B 21/4005; A41B 13/06
See application file for complete search history.

(56) References Cited

U.S. PATENT DOCUMENTS 2,225,884 A    12/1940  Parks
2,230,292 A     2/1941  Hilby
(Continued)

FOREIGN PATENT DOCUMENTS

GB       2466944 A     7/2010
KR    200312695 Y1    5/2003
(Continued)

OTHER PUBLICATIONS

International Search Report and Written Opinion from International Application No. PCT/US2022/0309907 dated Aug. 22, 2022.

*Primary Examiner* — Carrie R Dorna
*Assistant Examiner* — Joshua Daryl D Lannu
(74) *Attorney, Agent, or Firm* — Lando & Anastasi, LLP

(57)     ABSTRACT

A wearable weighted apparatus is capable of providing gentle, targeted pressure to an infant that can simulate the effect of being held by a caregiver. The wearable weighted apparatus comprises a textile base, and includes one or more wraps with a weighted region. The textile base may take the form of a conventional infant garment, or may take other forms such as a band or harness. When an infant is wearing the wearable weighted apparatus, the wrap may be extended across the infant's body such that the weighted region is positioned adjacent to a specific area of the infant's body, for example, the infant's chest. The weighted region may contain a filling that is slightly denser than the surrounding material, in order to provide gentle pressure to mimic the weight offered by a human hand or arm resting on a baby. The weighted region may have also dimensions designed to simulate the approximate size of a human hand, thus simulating the sensation of being held by a caregiver.

22 Claims, 9 Drawing Sheets

(51) Int. Cl.
A61M 21/00 (2006.01)
A63B 21/00 (2006.01)

(56) References Cited

U.S. PATENT DOCUMENTS

| | | | |
|---|---|---|---|
| 2,374,299 A | | 4/1945 | O'Hara |
| 2,578,323 A | | 12/1951 | Sillaway |
| 2,651,781 A | | 9/1953 | Buchholz |
| 2,675,557 A | | 4/1954 | Kempner |
| 3,259,126 A | | 7/1966 | Greiert |
| 3,845,513 A | | 11/1974 | Hubner |
| 3,965,487 A | | 6/1976 | Mazur |
| 4,611,353 A | | 9/1986 | Als et al. |
| 5,131,096 A | | 7/1992 | Olson |
| 5,144,694 A | * | 9/1992 | Conrad Da oud ... A63B 21/065 |
| | | | D2/737 |
| 5,722,094 A | | 3/1998 | Ruefer |
| 6,228,106 B1 | | 5/2001 | Simbruner et al. |
| 6,272,683 B1 | | 8/2001 | Symms et al. |
| 6,450,168 B1 | | 9/2002 | Nguyen |
| 6,692,413 B1 | * | 2/2004 | Greenberg ......... A63B 21/4001 |
| | | | 2/108 |
| 6,978,479 B2 | | 12/2005 | Thach |
| D513,357 S | | 1/2006 | Allard |
| 7,111,344 B2 | | 9/2006 | French |
| 7,181,789 B2 | | 2/2007 | Gatten |
| 7,587,769 B1 | | 9/2009 | McDermott |
| 7,673,354 B2 | | 3/2010 | Fader |
| 7,870,623 B2 | | 1/2011 | Judd |
| 8,095,994 B2 | | 1/2012 | Natonson et al. |
| 8,607,364 B2 | | 12/2013 | Barski |
| 8,695,133 B2 | | 4/2014 | Christensen et al. |
| 8,904,580 B1 | | 12/2014 | Christensen et al. |
| 8,943,615 B2 | | 2/2015 | Howard et al. |
| D728,198 S | | 5/2015 | Barski |
| 10,583,028 B2 | | 3/2020 | Gibson-Horn |
| 2002/0188999 A1 | | 12/2002 | Haar et al. |
| 2003/0131411 A1 | | 7/2003 | Gibson |
| 2006/0016005 A1 | | 1/2006 | Roda |
| 2006/0064794 A1 | * | 3/2006 | Howard ............... A41B 13/065 |
| | | | 2/69 |
| 2006/0090240 A1 | | 5/2006 | McKenzie et al. |
| 2007/0028387 A1 | | 2/2007 | Mathis |
| 2007/0113339 A1 | | 5/2007 | Field et al. |
| 2008/0105269 A1 | | 5/2008 | Rhodes |
| 2009/0064390 A1 | | 3/2009 | Beiring et al. |
| 2009/0099632 A1 | | 4/2009 | Krier |
| 2011/0179546 A1 | | 7/2011 | Millette et al. |
| 2011/0180079 A1 | | 7/2011 | Krawchuk |
| 2011/0197365 A1 | | 8/2011 | Wadia |
| 2012/0284922 A1 | * | 11/2012 | Gangan ................. A41B 13/06 |
| | | | 5/494 |
| 2013/0139290 A1 | | 6/2013 | Barski |
| 2013/0269080 A1 | | 10/2013 | Parker |
| 2013/0333113 A1 | | 12/2013 | Gotel et al. |
| 2015/0000036 A1 | | 1/2015 | Krawchuk |
| 2016/0128392 A1 | | 5/2016 | Krawchuk |
| 2020/0196685 A1 | * | 6/2020 | Williams ............. A47G 9/0223 |
| 2021/0059319 A1 | | 3/2021 | Karp et al. |

FOREIGN PATENT DOCUMENTS

| | | | |
|---|---|---|---|
| WO | 2007098558 A1 | 9/2007 | |
| WO | 2016038101 A1 | 3/2016 | |

* cited by examiner

WEARABLE WEIGHTED APPARATUS

BACKGROUND

Studies in infant care suggest the importance of physical touch from a parent or caregiver. The sensation of physical touching is perceived by an infant as a comforting and reassuring indication, and results in physiologic changes exhibited by the infant. Touching sensations that result from cradling may facilitate the onset of sleep.

The historical practice of swaddling, particularly the gentle binding of an infant's arms close to the body, has been found to help infants go to sleep faster and stay asleep longer by simulating the sensation of being held by a caregiver. However, swaddling is a technique that requires training and practice to employ. There may be risks to an infant when swaddled incorrectly, including the risk of hip dysplasia if the infant's legs are bound too tightly.

A need exists for a garment or apparatus capable of providing gentle, targeted pressure to an infant that can simulate the effect of being held by a caregiver.

SUMMARY

This disclosure is directed to wearable apparatus for infants that include one or more wraps with a weighted region. In one embodiment, the wearable apparatus comprises a wrap comprised of a flexible textile base, constructed of either natural or synthetic material, or a combination of both, that may be affixed to the wearable apparatus on one side of the wrap. The wrap is comprised of fabric, and includes a weighted region that has a mass greater than the fabric. When an infant is wearing the wearable apparatus, the wrap may be extended across the infant's body such that the weighted region is positioned adjacent to a specific area of the infant's body, for example, the infant's chest. The greater mass from the weighted region adjacent the infant's body is configured to mimic the sensation of being held by a caregiver, helping the infant go to sleep faster, and stay asleep longer.

The wrap may further comprise additional features. For example, in one embodiment, the wrap includes a second side of the wrap that is substantially opposite to the side of the wrap that is attached to the wearable apparatus, that is configured for removable attachment to the apparatus. The capability for removable attachment allows the wrap to be extended over the infant's body and secured in position so that the weighted region remains adjacent to the area of the infant's body in which it is intended to be placed. The wrap may also include one or more stretchable portions, utilizing a stretchable material such as elasticized cotton, that can be stretched as the wrap is extended over the infant's body, increasing the tension of the wrap against the wearable garment, and thereby the sensation of pressure felt by the infant.

In one embodiment, the wearable apparatus may comprise an infant garment, for example, infant bodysuits, swaddle suits, "footie" pajamas, rompers, tops, or similar styles of garment. In other embodiments, the wearable apparatus comprises a fabric band. The band may be configured for removable attachment to the wrap, forming a tube or cylindrical shape with a circumference that is equal to or greater than the circumference of an average infant's chest, which for a newborn may be roughly 12 to 13 inches.

In another embodiment, the wearable apparatus may comprise a plurality of belts attached to the wrap. This may include, for example, two belts configured to lay over an infant's shoulders, and a third belt configured to pass between the infant's legs. The belts may be configured such that one belt may be connected to another belt. When connected, the three belts form a harness designed to maintain the wrap in a desirable position on the infant's body.

The present disclosure also relates to different configurations of wraps and weighted regions. In one embodiment, the wrap comprises a plurality of weighted regions disposed across substantially the entire surface of the wrap. Alternatively, the wrap may comprise a single weighted region that is quilted or segmented, with the quilting or segmenting dividing the weighted region into a plurality of compartments.

In another embodiment, the wrap comprises one weighted region located in a specific part of the wrap, such as the center. The weighted region may have dimensions designed to simulate the approximate size of a human hand, between two inches and four inches in width and height.

In another embodiment, the wearable apparatus comprises a plurality of wraps, each wrap having a weighted region configured to place pressure at a specific area of the body of an infant wearing the garment, for example, the tops of the infant's arms, legs, and multiple regions of the infant's chest. The plurality of wraps may be attached to the wearable apparatus at different locations from one another. For example, an apparatus comprising two wraps may have one wrap attached to each of the apparatus's shoulders. And an apparatus designed to place pressure on the tops of an infant's arms or legs may be attached at points on the arms or legs of the apparatus. Some or all of the wraps may be attached to the apparatus at points that are non-concurrent with one another.

The weighted regions may contain a filler configured to apply a weight greater than that of the fabric alone, such as poly beads, Styrofoam beads, hypoallergenic material, memory foam, micro foam beads, polystyrene, polyfiber, walnut shells or buckwheat. In one embodiment, the weighted region contains an amount of filler designed to mimic the sensation of a human hand resting on the baby, for example, between about 0.25 lbs and 1 lbs.

The wrap may be attached to the wearable apparatus in different ways. In one embodiment, the wrap is permanently attached to the wearable apparatus, such as by stitching it into the apparatus, at a position substantially on the side of the apparatus near the wearer's torso. Thus, when the wrap is extended over the front of the apparatus, the weighted region is in a position adjacent to the center of the infant's chest. In another embodiment, the wrap is attached to wearable apparatus at the bottom of the apparatus, so that the wrap when folded over the apparatus operates as a blanket. In another embodiment, the wrap is attached to the wearable apparatus at two points near the shoulders of the apparatus, so that the wrap may be extended across the front of the apparatus like a bib. In another embodiment, the wrap is removably affixed to the wearable apparatus, such as by hook-and-loop fasteners. Thus, the wrap may be removed when it is not time for the infant to sleep, allowing the wearable apparatus to be used as daywear, without the additional encumbrance of the wrap.

DETAILED DESCRIPTION

Figure 1:
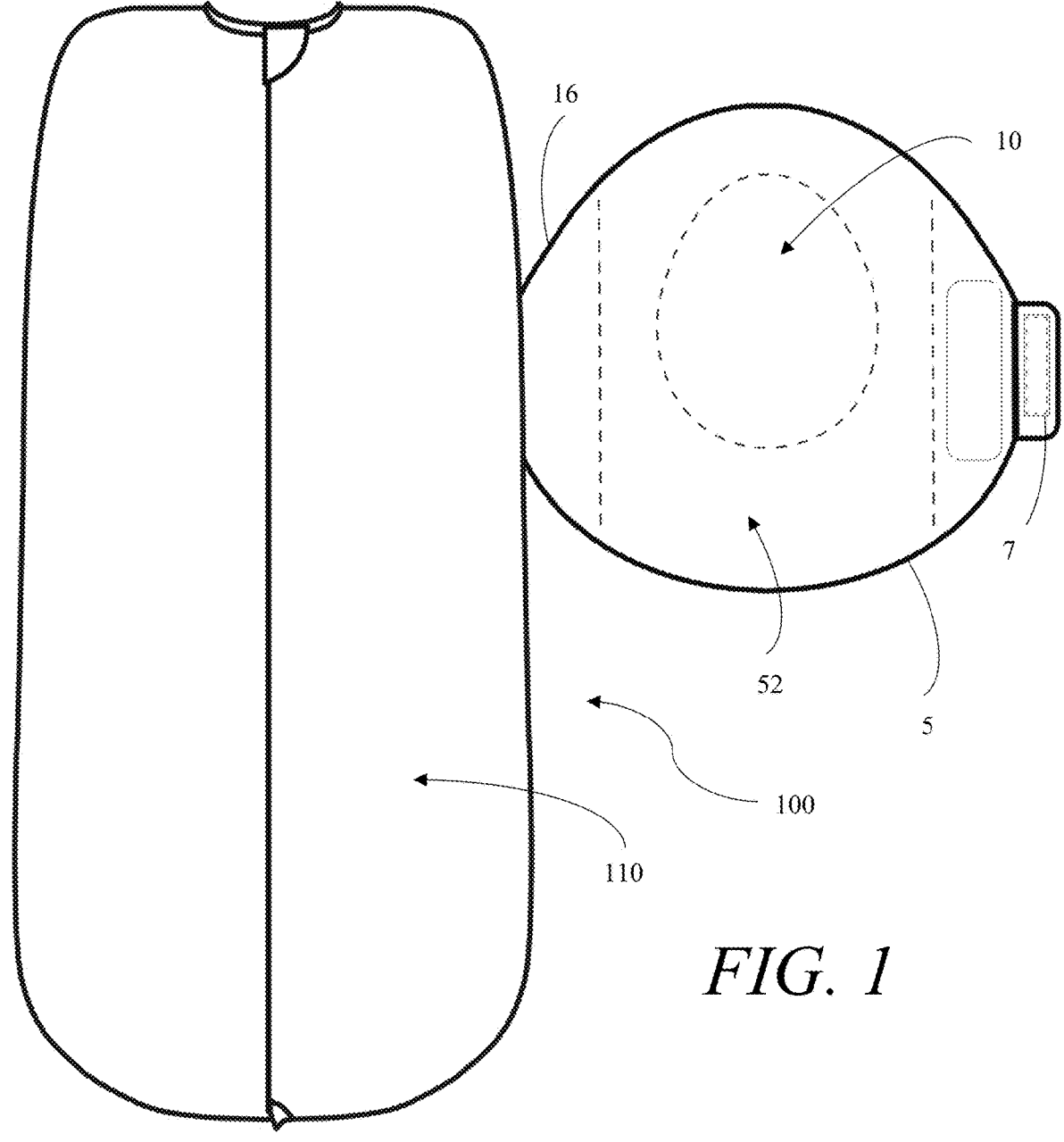
FIG. 1 is a front perspective view of a wearable apparatus with a wrap.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Soon after birth, many infants experience difficulty sleeping or resting when they are not being held by their caregivers. When an infant is held by a caregiver, gentle pressure applied by the caregiver's arms and body lulls the infant into sleep.

Embodiments of the present disclosure include infant garments and apparatuses with weighted regions designed to apply gentle pressure over targeted areas of an infant's body. These weighted regions simulate the gentle pressure of being held by a caregiver, helping an infant go to sleep faster, and stay asleep longer.

Figure 2:
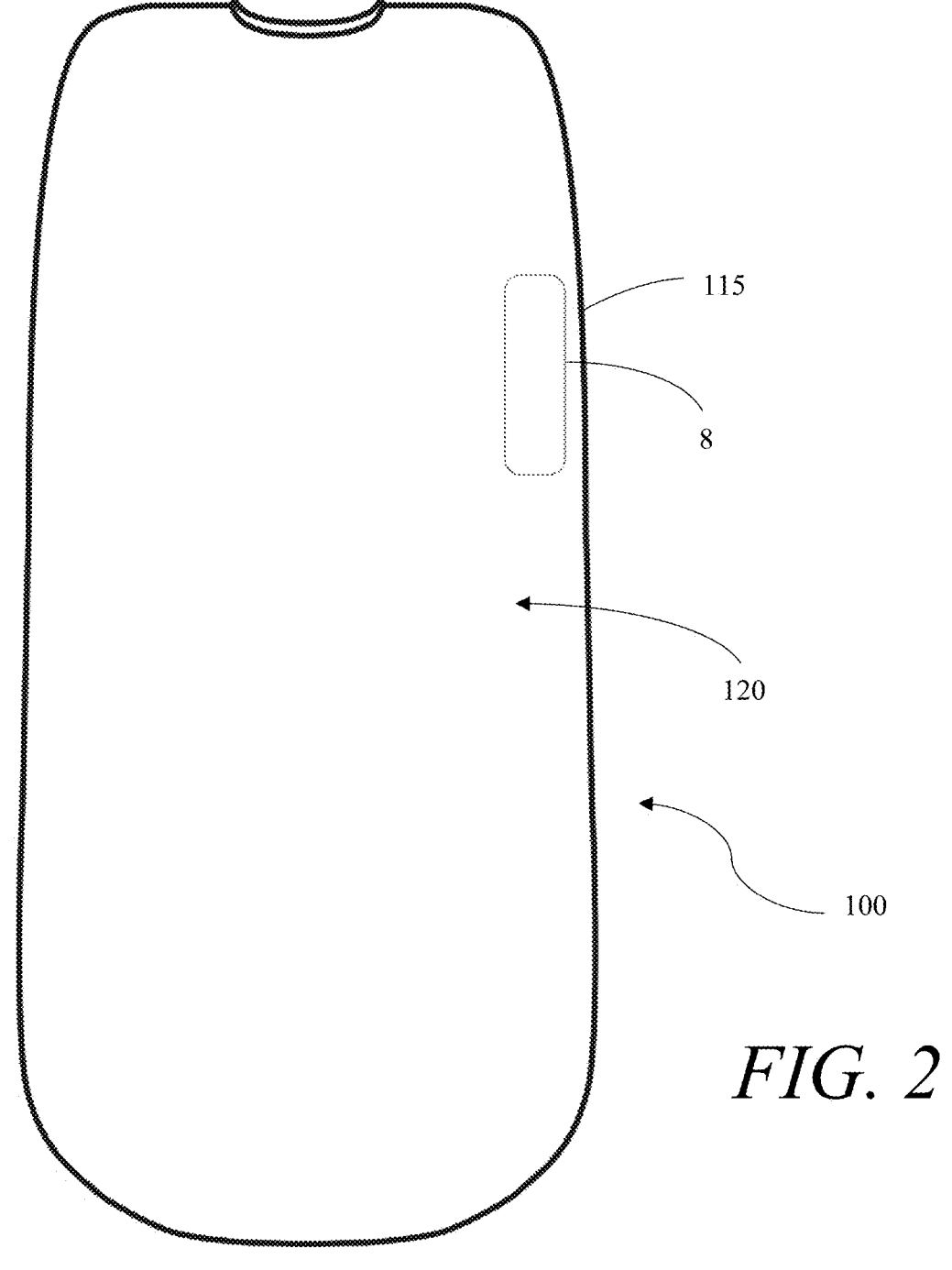
FIG. 2 is a rear perspective view of a wearable apparatus.

Referring to FIGS. 1 and 2, a wearable apparatus 100 is shown with a wrap 5 that includes a weighted region 10. Wearable apparatus 100 includes a front panel 110 and a back panel 120, each of which may be comprised of one or more pieces of fabric attached to one another through any acceptable means known in the art, including stitching. The fabric may be comprised of any material suitable for constructing infant clothing, including natural or synthetic material, or a combination of both. Front panel 110 and back panel 120 may be attached to one another at an edge region of the respective panels, forming a garment having an internal compartment suitable for an infant's body.

Wearable apparatus 100 may be a full body length garment configured to retain an infant's arms and legs in a single compartment. Wearable apparatus 100 may include wrap 5, including one or more weighted regions 10. Wrap 5 with a weighted region can be incorporated on, or used with, a variety of infant garments, including infant bodysuits, swaddle suits, "footie" pajamas, rompers, tops, or similar styles of garment known in the art. Wrap 5 may extend around a portion of wearable apparatus 100, including a portion of front panel 110. Wrap 5 may have a circular, oval, egg, square, or rectangular shape, among other shapes. Wrap 5 has a front portion 51 and back portion 52.

Wrap 5 may include a weighted region 10. Weighted region 10 may encompass part or all of wrap 5. Weighted region 10 may be attached to wrap 5 on the front portion 51 or rear portion 52 in any known way, including sewing the weighted region 10 onto or into wrap 5. Wrap 5 may include one or more layers of fabric. Two or more layers may be attached to one another by any suitable mechanism, such as stitching. The plurality of layers of fabric may form an internal area in which weighted region 10 is disposed.

Weighted region 10 defines a region of increased mass or bulk relative to the fabric, for providing increased pressure on an infant wearing wearable apparatus 100. Weighted region 10 may be of various shapes and sizes. In some examples, weighted region 10 may have a generally circular, oval, egg, square, or rectangular shape, among other shapes.

Weightiness or firmness of weighted region 10 may be created by using a filling that is slightly denser than the surrounding material, for example plastic pellets. Alternative weighted fillings may comprise poly beads, Styrofoam beads, hypoallergenic material, memory foam, micro foam beads, polystyrene, and/or various organic materials such as walnut shells or buckwheat. Such a filling may offer a gentle pressure, and move with the baby's movements. The weight offered by weighted region 10 may be designed to mimic the weight offered by a human hand or arm a resting baby, for example it can be approximately 0.25 to 1 lbs, or 1 to 5 lbs. The density of the weighted filling may be chosen to allow it to be flexible so that it takes the desired shape and position. Alternatively, fibrous filling such as polyester may also be employed. It is to be understood that various configurations of different weighted filing materials and different placements and spacing of these materials within weighted region 10 are within the scope of the disclosure herein.

The shape of weighted region 10 or distribution of filler in weighted region 10 may be designed to mimic the shape of a human hand or arm. For example, weighted region 10 may have a width and length of between 3 to 5 inches, or a width and length of 2 inches and 8 inches. Alternatively, the weighted region may comprise a plurality of compartments having filler, which provide more irregular or more distributed pressure across a larger area, consistent with the irregular pressure that an infant may feel while being held. It is to be understood that various configurations of different sizes and distributions of the weighted region are within the scope of the disclosure herein and the specific disclosed embodiments are not intended to be limiting.

Wrap 5 may be permanently affixed to wearable apparatus 100 such as by stitching. In one embodiment shown in FIG. 1, wrap 5 may be affixed to wearable apparatus 100 at the interface 115 between the front panel 110 and the back panel 120. Wrap 5 may also be affixed to a specific location either on back panel 120, or front panel 110. For example, by attaching wrap 5 at a location on front panel 110, it may minimize the amount of fabric required for wrap 5 to cover the relevant area of the infant's body when it is extended over the infant. This could have the further advantage of minimizing the risk that the wrap will become tangled on itself or with the infant's bedding. In another embodiment, the wrap may be affixed to back panel 120 of wearable apparatus 100. In this configuration, the wrap and its affixation point may be hidden from view when the wrap is not extended across the front of the infant. By affixing the wrap to the back, the infant's own weight can help keep the wrap in position when the infant is lying on its back and wrap 5 is extended across its chest.

Alternatively, wrap 5 may be removably affixed to the wearable apparatus 100 by any suitable mechanism, including zippers, hook-and-loop fasteners, buttons, snaps, magnets, or elastic bands.

Figure 3:
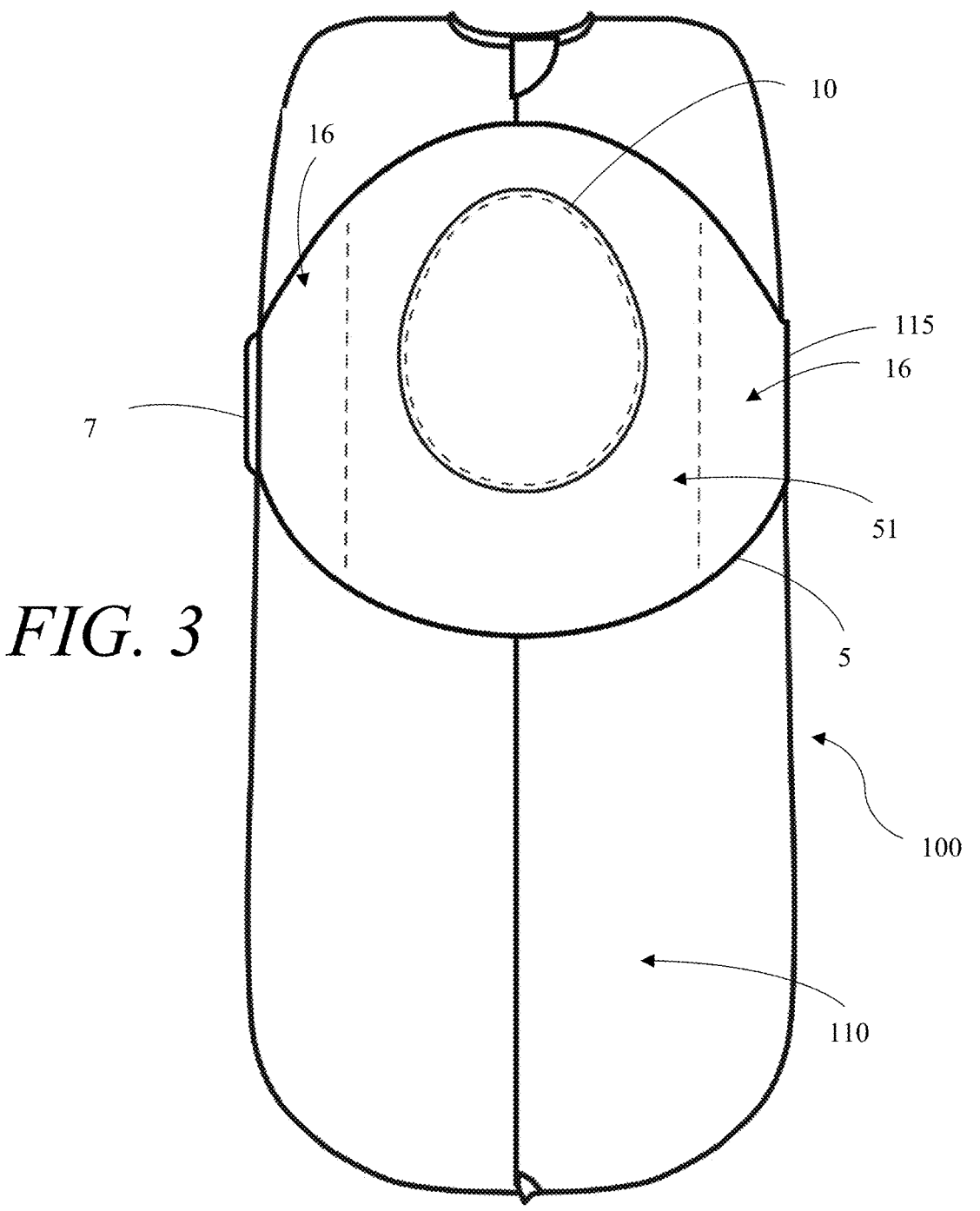
FIG. 3 is a front perspective view of a wearable apparatus with a wrap.

Referring to FIG. 3, wrap 5 may include an attachment mechanism 7, for securing an end of wrap 5 when it is extended around front panel 110. Turning to FIG. 2, attachment mechanism 7 is configured to engage with a corresponding attachment mechanism 8 on the back panel 120 of wearable apparatus 100. In the example arrangement, the attachment mechanism 7 and the corresponding attachment mechanism 8 are hook-and-loop fasteners. Alternatively, any suitable mechanism of removable attachment may be used, including zippers, buttons, snaps, or magnets. Wrap 5 may include multiple corresponding attachment mechanisms 8 to allow wrap 5 to be used in different positions or have different tensions.

In other embodiments, wrap 5 may not include an attachment mechanism 7, and may instead rely on the weight of wrap 5 to remain in position and resist being dislodged by the normal movements of the infant. It may be advantageous to allow the infant to dislodge the wrap in the event that the additional weight or insulation provided by the fabric of the wrap becomes uncomfortable. In this example configuration, wrap 5 is sized such that an infant is unlikely to become tangled in wrap 5, or cause the fabric of wrap 5 to cover the infant's nose or mouth. This may be accomplished by ensuring that wrap 5, when measured from the affixation point to the most distal end of wrap 5, is no longer than the distance from affixation point to the infant's nose and mouth.

As shown in FIG. 3, in some embodiments, wrap 5 may include stretchable portions 16, which may be made from elasticized cotton, spandex, or other stretchable materials known in the art to be suitable for use with infant clothing. Stretchable portions 16 may be located on one or both ends of wrap 5. In other embodiments, stretchable portions 16 may cover the entire wrap 5. Stretchable portions 16 may help wrap 5 remain in position, resist being thrown off of the infant in the course of the infant's normal movements. In some embodiments, stretchable portions 16 can be stretched to increase the tension of wrap 5 against the infant's body, thereby increasing the pressure applied to infant's body by weighted region 10.

Extending wrap 5 around front panel 110 orients weighted region 10 in the chest region of the infant. In this position, weighted region 10 engages against the infant by application of pressure simulating the touch of a caregiver.

Figures 4A, 4B:
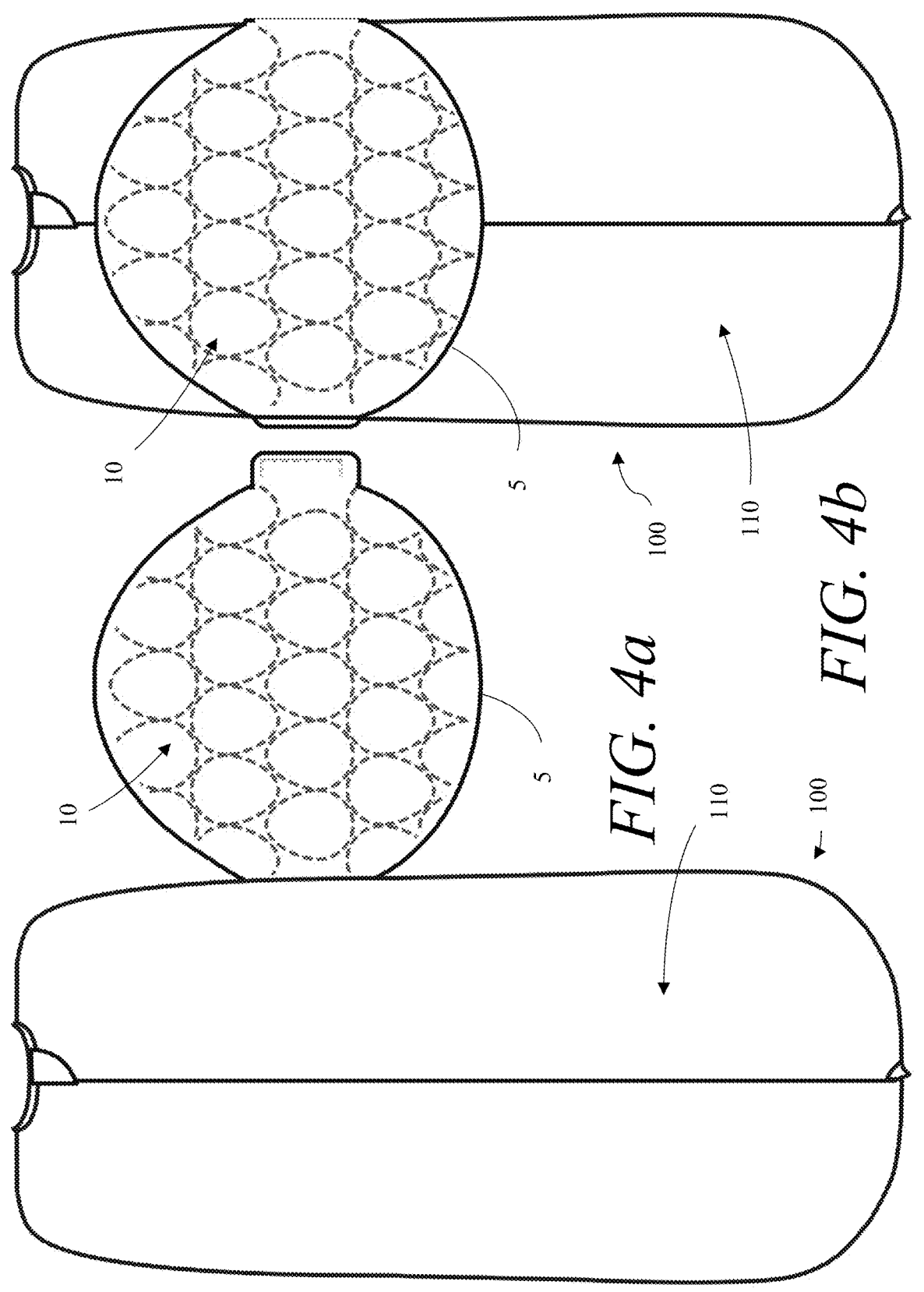
FIG. 4*a* is a front perspective view of a wearable apparatus with a wrap.
FIG. 4*b* is a front perspective view of a wearable apparatus with a wrap.

FIGS. 4a and 4b show another embodiment of the present disclosure. In this embodiment, a plurality of weighted regions 10 are disposed on or within wrap 5. Weighted regions 10 are disposed within plurality of compartments, each of the compartments including a portion of weighting filling. The plurality of compartments may be of equal size, or in alternative arrangements, they may be of varying sizes and shapes, including circular, oval, egg, square, or rectangular shape, among other shapes. Weighted regions 10 may distribute the additional mass or bulk across a larger area of the infant's torso.

Figures 5A, 5B:
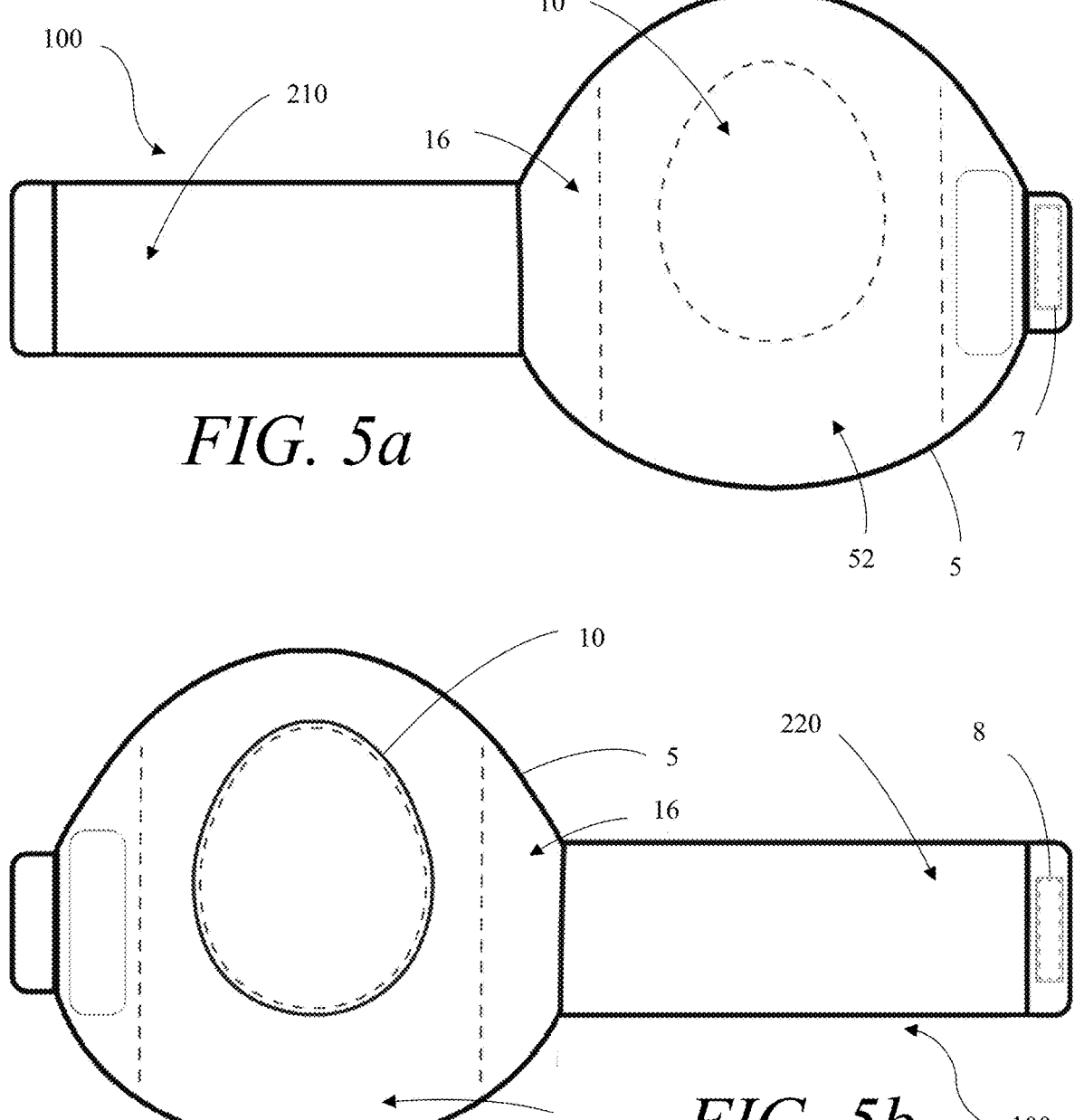
FIG. 5*a* is a front perspective view of a wearable apparatus with a wrap.
FIG. 5*b* is a rear perspective view of a wearable apparatus with a wrap.

FIGS. 5a and 5b show wearable apparatus 100 that does not comprise a garment. In this configuration, wearable apparatus 100 is in the shape of a band of fabric, and includes a front side 210 and a back side 220, which may be comprised of a single piece of fabric, or multiple pieces of fabric attached to one another through any acceptable means known in the art, including stitching. Wearable apparatus 100 may be configured to be placed around the infant, with the front side 210 adjacent to the infant's back, such that wrap 5 may wrap over the front of the infant's torso. Wrap 5 may be secured in place by joining attachment mechanism 7 on wrap 5 to the corresponding attachment mechanism 8 located on the substantially opposite side of wearable apparatus 100 from the location in which wrap 5 is attached to the wearable apparatus 100, forming a cylindrical shape around the infant's torso. Wrap 5 may include weighted region 10 and stretchable portion 16. Weighted region 10 may have various shapes and sizes, including circular, oval, egg, square, or rectangular shape, among other shapes. Weighted region 10 may have a width and length of between 3 to 5 inches, or a width and length of 2 inches and 8 inches. Wrap 5 may be coextensive in size and shape with weighted region 10. Or wrap 5 may have a greater length and width than weighted region 10.

Figure 6:
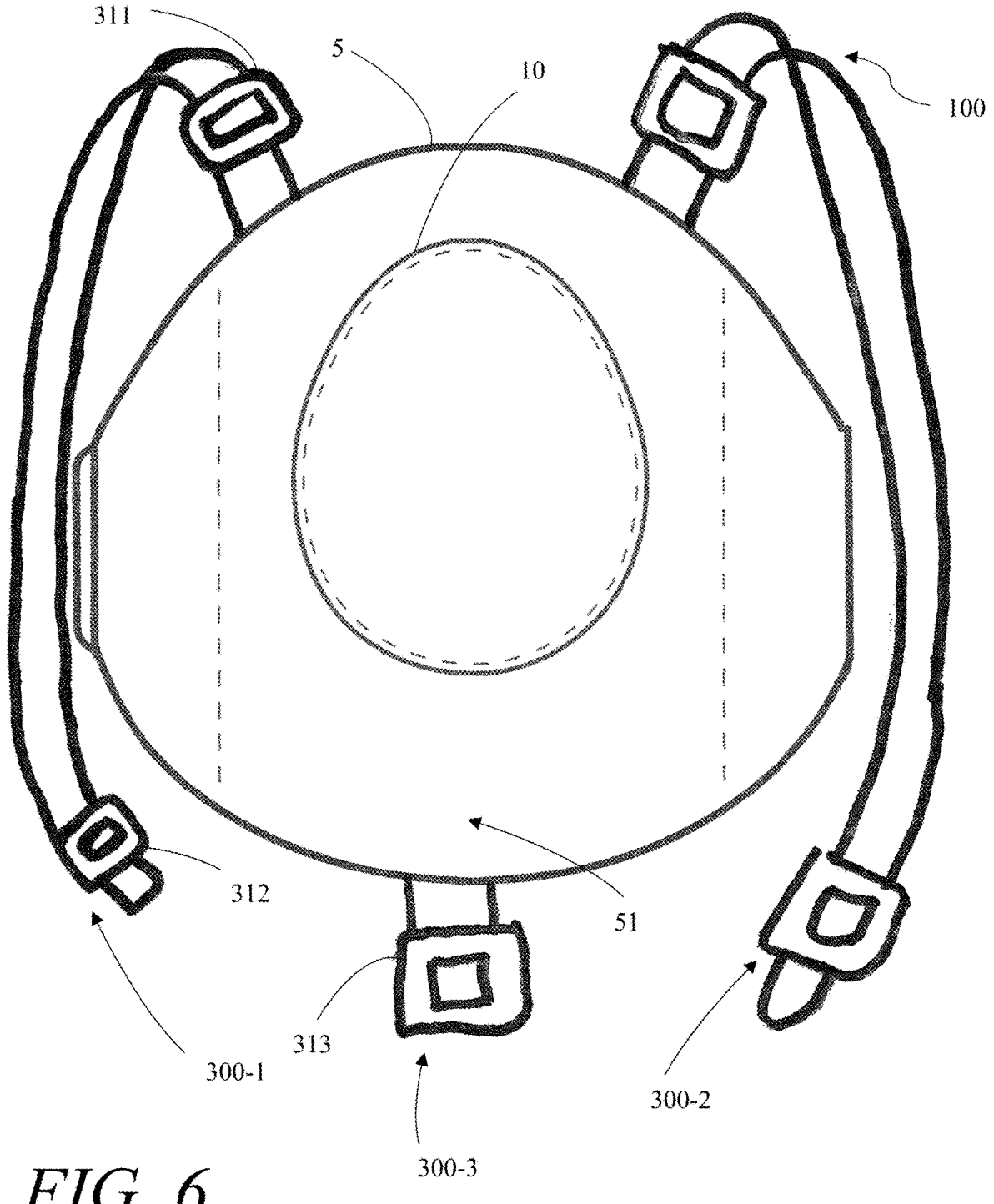
FIG. 6 is a front perspective of a wearable apparatus with a wrap.

FIG. 6 shows wearable apparatus 100 with a wrap and harness. In this configuration, wearable apparatus 100 includes a plurality of belts 300-1, 300-2 and 300-3 extending from attachment points on wrap 5. Each of belts 300-1, 300-2 and 300-3 may be constructed of Nylon webbing, elasticated cotton, or other types of materials known in the art to be useful in the construction of seatbelts, belts, or suspenders. Each of said belts may further include a length adjustor 311 for adjusting the length of said belt, for example, a slide buckle; and, each of said belts may terminate in either a male connector 312, such as a seatbelt clip, or a female connector 313, such as a buckle. Each of said belts may include hook and loop fasteners to attach to wearable apparatus 100 or other belts. Wearable apparatus 100 may be configured so that wrap 5 may be positioned on the infant where it is desirable, such as the center of the infant's chest, with belt 300-1 and 300-2 extending over the infant's shoulders, and belt 300-3 extending between the infant's legs. The individual belts 300-1, 300-2 and 300-3 may be attached to one another by joining male connector 312 with female connector 313, forming a harness around the infant capable of maintaining wrap 5 in the desirable location. In this configuration, wearable apparatus 100 is configured to apply gentle pressure to an infant at a specific point on the infant's body without regard to the type of clothing worn by the infant. The present embodiment shows a harness having 3 belts. However, it is to be understood that various configurations of belts may be employed without departing from the present disclosure, including a wearable apparatus 100 comprised of 2-belts, 5-belts, or other numbers of belts known in the art to be useful for restraining an infant. Wrap 5 may include weighted region 10 and stretchable portion 16. Weighted region 10 may have various shapes and sizes, including circular, oval, egg, square, or rectangular shape, among other shapes. Weighted region 10 may have a width and length of between 3 to 5 inches, or a width and length of 2 inches and 8 inches. Wrap 5 may be coextensive in size and shape with weighted region 10. Or wrap 5 may have a greater length and width than weighted region 10.

Figure 7:
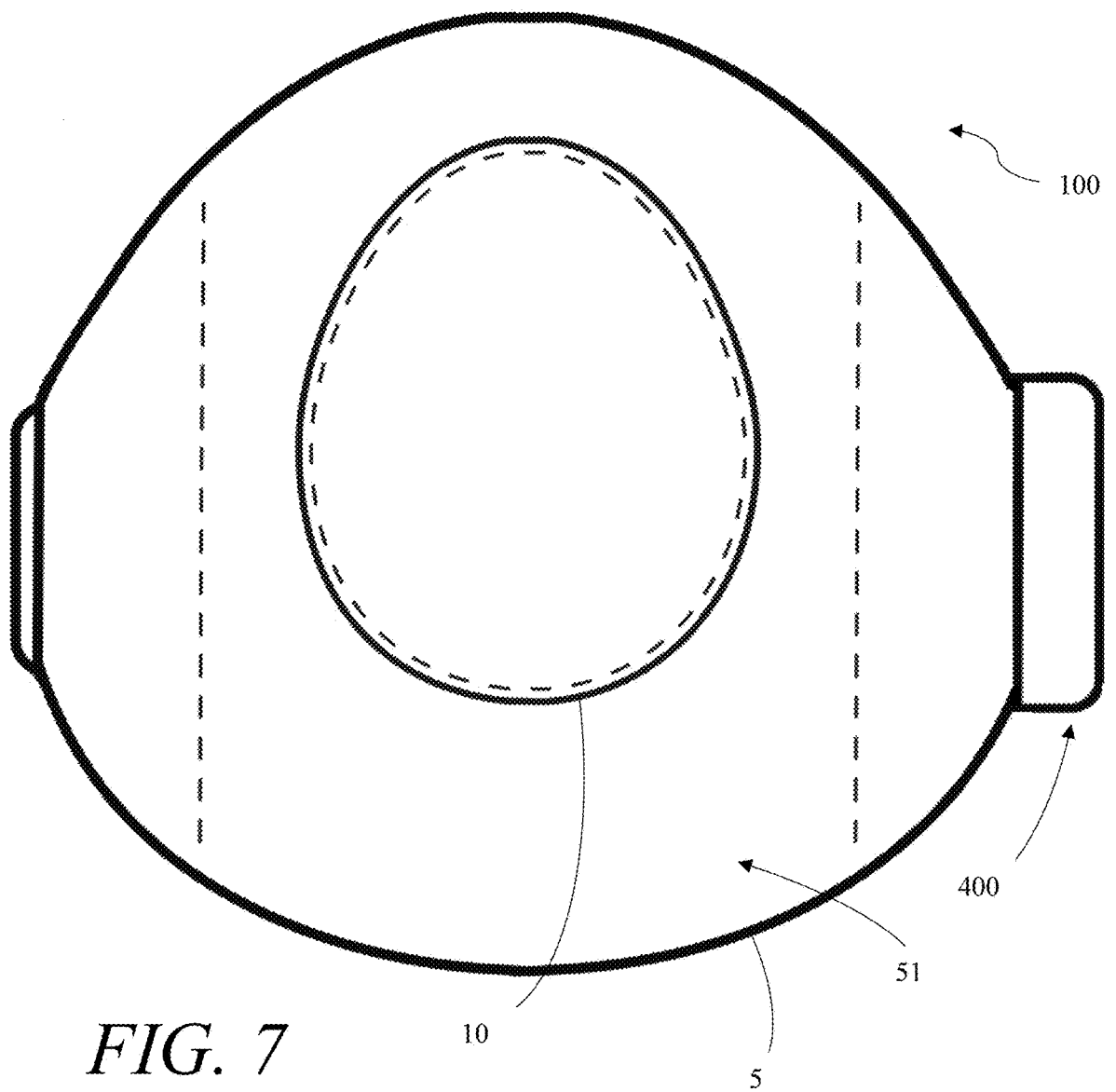
FIG. 7 is a front perspective of a wrap.

FIG. 7 shows an embodiment of the present invention in which wearable apparatus 100 includes a wrap 5 and an attachment piece 400. In this configuration, attachment piece 400 extends from an attachment point on wrap 5. The attachment piece includes a means of attaching the wrap to a compatible infant garment, for example, hook and loop fasteners, buttons, snaps, or a zipper. A compatible infant garment may be a garment that has been specifically designed to attach wearable apparatus 100 via attachment piece 400. Wrap 5 may include weighted region 10 and stretchable portion 16. Weighted region 10 may have various shapes and sizes, including circular, oval, egg, square, or rectangular shape, among other shapes. Weighted region 10 may have a width and length of between 3 to 5 inches, or a width and length of 2 inches and 8 inches. Wrap 5 may be coextensive in size and shape with weighted region 10. Or wrap 5 may have a greater length and width than weighted region 10.

Figures 8, 9:
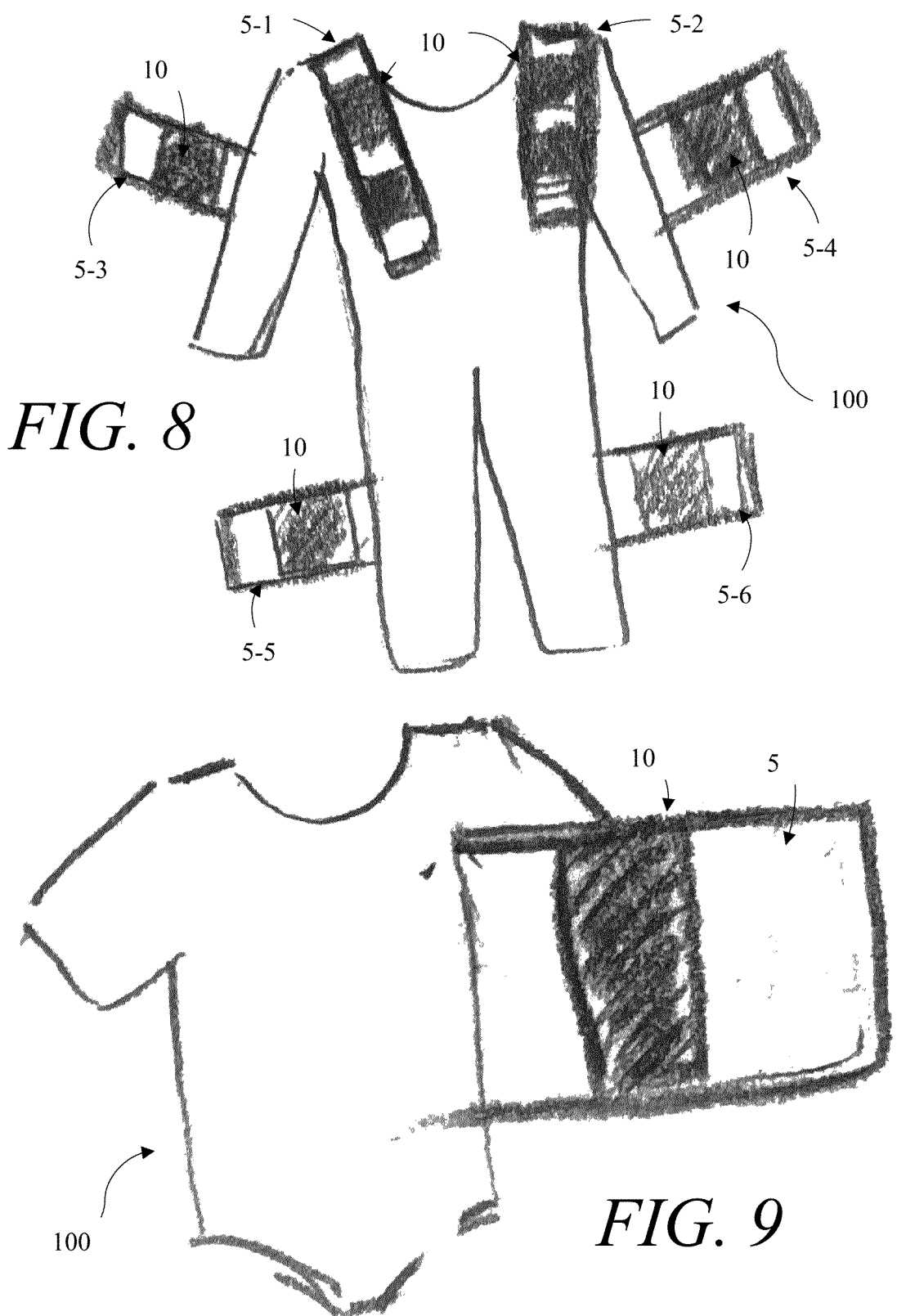
FIG. 8 is a front perspective of a wearable apparatus with a plurality of wraps.
FIG. 9 is a front perspective of a wearable apparatus with a wrap.

FIG. 8 shows an embodiment of the present disclosure having a plurality of wraps 5. Chest wraps 5-1 and 5-2 may be attached to wearable apparatus 100 near the shoulder regions, and may be configured to wrap over the infant's shoulders to position weighted region 10 on top of the infant's chest. Arm wraps 5-3 and 5-4 may be attached to wearable apparatus 100 near the arm regions, and may be configured to wrap around a portion of the infant's arm. Arm wraps 5-3 and 5-4 may form a cuff in which the weighted regions 10 rest on top of the infant's bicep. Leg wraps 5-5 and 5-6 may be attached to wearable apparatus 100, and may be configured to wrap around a portion of an infant's leg. Leg wraps 5-5 and 5-6 may form a cuff, in which the weighted regions rest on top of the infant's thigh. It is to be understood that the number and positioning of wraps 5 and weighted regions 10 are exemplary, and that various configurations of wraps are within the scope of this disclosure. Each of wraps 5-1, 5-2, 5-3, 5-4, 5-5, and 5-6 may be permanently or releasably attached to wearable apparatus 100, and each wrap 5 may attach to itself or other wraps. Each wrap 5 may be removed from wearable apparatus 100 and placed in different locations on wearable apparatus 100.

FIG. 9 shows an alternate embodiment in which wearable apparatus 100 is a bodysuit. Wrap 5 may be attached to wearable apparatus 100 on the front, side or back of wearable apparatus 100. Wrap 5 may include a weighted region 10 designed to cover a portion of an infant's chest. Weighted region 10 may have various shapes and sizes, including circular, oval, egg, square, or rectangular shape, among other shapes. The distribution of filler within weighted region 10 may be uniform or segmented, such as to provide more filler in the center and less filler at the ends of weighted region 10.

Figures 10, 11:
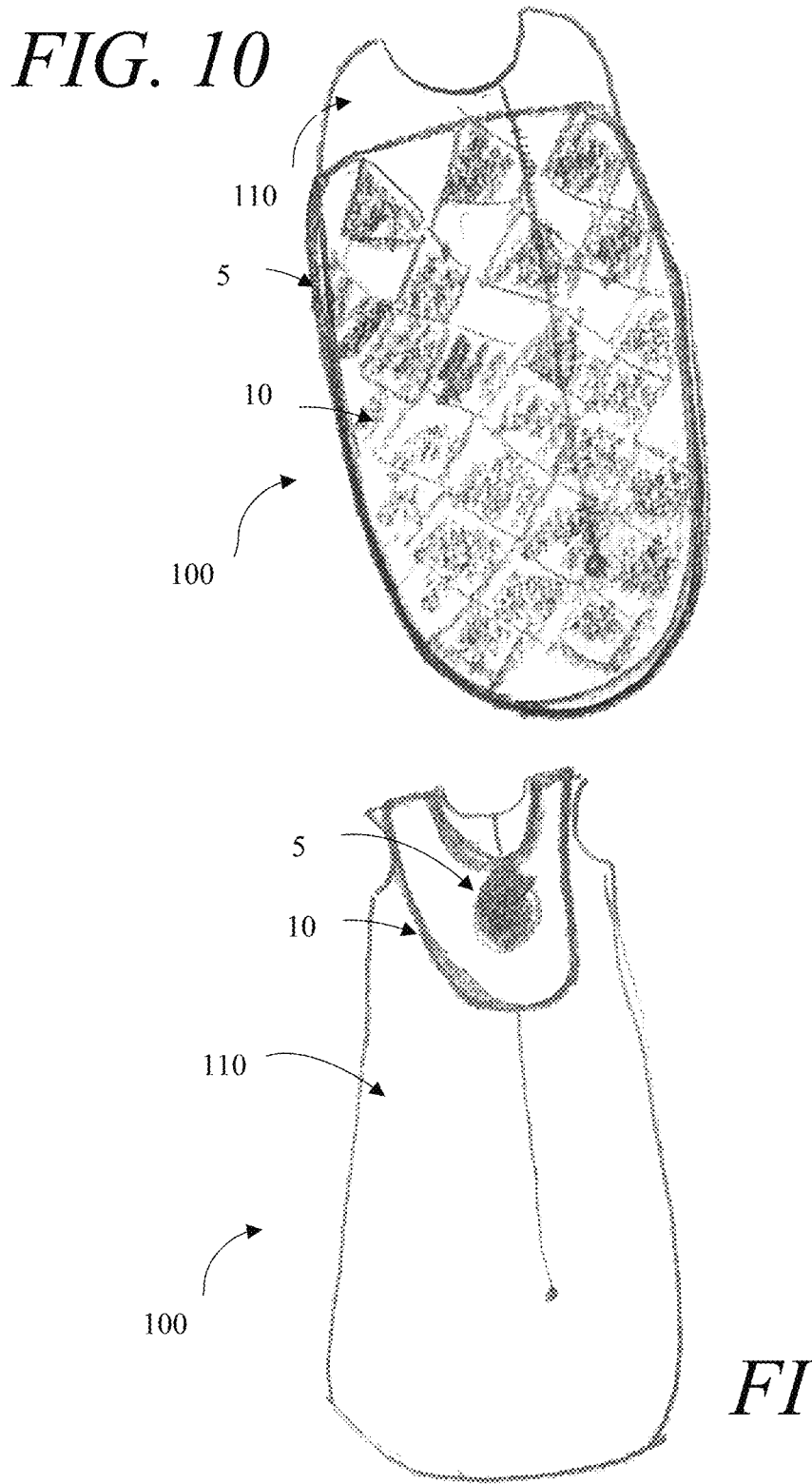
FIG. 10 is a front perspective of a wearable apparatus with a wrap.
FIG. 11 is a front perspective of a wearable apparatus with a wrap.

FIG. 10 shows another embodiment of the present disclosure in which wrap 5 covers a majority of wearable apparatus 100. Weighted regions 10 may be distributed around wrap 5 in a quilted pattern. Weighted regions 10 may be distributed to only cover specific portions of the infant, such as the chest, arms, or legs. Wrap 5 may be sized to cover the entire torso and lower body region of wearable apparatus 100. Wrap 5 may be attached to wearable apparatus 100 on the front, back or side of wearable apparatus 100. Wrap 5 may be removable, allowing it to be applied or removed as needed. For example, wrap 5 may be applied when an infant is sleeping and removed when an infant is awake.

FIG. 11 shows another embodiment of the present disclosure in which wrap 5 may be in the style of a bib. In this configuration, wrap 5 can be removably attached to wearable apparatus 100 near the apparatus's shoulders and extends across the infant's chest on front panel 110, with a hole in the center of wrap 5 provided for the infant's head. Wrap 5 may comprise a single piece or multiple pieces, each removably attached to wearable apparatus 100 at or near one of the garment's shoulders. The multiple pieces of wrap 5 may be connected to one another at one or more locations on the infant's chest, forming a single bib-like structure. Wrap 5 may include one or more weighted regions 10. Wrap 5 can be positioned such that weighted region 10 lays substantially in the center of the infant's chest while it is being worn.

Having now described some illustrative embodiments, it is apparent that the foregoing is illustrative and not limiting, having been presented by way of example. In particular, although many of the examples presented herein involve specific combinations of elements, those elements may be combined in other combinations. Elements and features discussed only in connection with one embodiment are not intended to be excluded from other embodiments.

Any references to front and back, left and right, top and bottom, or upper and lower and the like are intended for convenience of description, not to limit the present systems and methods or their components to any one positional or spatial orientation.

Any references to embodiments or elements herein referred to in the singular may also embrace embodiments including a plurality of these elements, and any references in plural to any embodiment or element herein may also embrace embodiments including only a single element. References in the singular or plural form are not intended to limit the presently disclosed components or elements to single or plural configurations.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature or characteristic described in connection with the embodiment may be included in at least one embodiment. Such terms as used herein are not necessarily all referring to the same embodiment. Any embodiment may be combined with any other embodiment, inclusively or exclusively, in any manner consistent with the aspects and embodiments disclosed herein.

What is claimed:

1. A wearable apparatus, comprising:
a textile base; and
a wrap formed from a separate piece of fabric from the textile base, the wrap having a first side attached to the textile base and a second side configured to be secured across the textile base, wherein the wrap comprises one or more weighted regions having a mass greater than the fabric of the wrap, and wherein each weighted region is disposed entirely within the wrap; and
a plurality of belts attached to the wrap, wherein a first belt of the plurality of belts attaches to a second belt of the plurality of belts to secure the wrap over the textile base.

2. The wearable apparatus of claim 1, wherein the second side is substantially opposite to the first side, and configured for removable attachment to the wearable apparatus.

3. The wearable apparatus of claim 1, wherein the textile base comprises a band having a first side attached to the wrap, and a second side substantially opposite to the first side, configured for removable attachment to the wrap.

4. The wearable apparatus of claim 3, wherein the textile base and the wrap have a length that is equal to or greater than 12 inches.

5. The wearable apparatus of claim 1, wherein the one or more weighted region comprises a filler.

6. The wearable apparatus of claim 5, wherein the filler comprises of one or more of poly beads, expanded polystyrene (EPS) beads, hypoallergenic material, memory foam, micro foam beads, polystyrene, polyfiber, walnut shells or buckwheat.

7. The wearable apparatus of claim 1, wherein the one or more weighted region comprises a plurality of compartments, wherein each compartment includes filler.

8. The wearable apparatus of claim 7, wherein at least one compartment of the plurality of compartments includes more filler than a different compartment of the plurality of compartments.

9. The wearable apparatus of claim 1, wherein a length and a width of the one or more weighted region is substantially coextensive with a length and a width of the wrap.

10. The wearable apparatus of claim 1, wherein the one or more weighted region is located substantially in a center of the wrap.

11. The wearable apparatus of claim 1, wherein the textile base and wrap are configured to releasably engage with one another.

12. The wearable apparatus of claim 1, wherein the one or more weighted region has a width of 2 inches and a length of 4 inches.

13. The wearable apparatus of claim 1, wherein the attachment of one side of the wrap to the textile base is a permanent attachment.

14. The wearable apparatus of claim 1, wherein the textile base is a garment for infants.

15. The wearable apparatus of claim 1, wherein the one or more weighted region does not contain a filler.

16. A wearable apparatus, comprising:

a fabric base; and a plurality of wraps, each wrap formed from a separate piece of fabric from the fabric base and having a side attached to the fabric base, wherein each wrap comprises one or more weighted regions having a mass greater than the fabric of the wrap, and wherein each weighted region is disposed entirely within the corresponding wrap; and a plurality of belts attached to the plurality of wraps, wherein a first belt of the plurality of belts attaches to a second belt of the plurality of belts to secure at least one wrap of the plurality of wraps over the fabric base.

17. The wearable apparatus of claim 16, wherein the side of each wrap of the plurality of wraps is removable from the fabric base.

18. The wearable apparatus of claim 16, wherein the fabric base includes a shoulder region and at least one wrap of the plurality of wraps is attached to the shoulder region of the fabric base.

19. The wearable apparatus of claim 18, wherein the fabric base includes an arm region and at least one wrap of the plurality of wraps is attached to the arm region of the fabric base.

20. The wearable apparatus of claim 16, wherein at least one weighted region of the one or more weighted regions is located substantially in a center of each wrap.

21. The wearable apparatus of claim 16, wherein a length and a width of at least one weighted region of the one or more weighted regions is substantially coextensive with a length and a width of each wrap.

22. A wearable apparatus, comprising:

a fabric base;

a wrap formed from a separate piece of fabric from the fabric base, the wrap comprising fabric and one or more weighted regions having a mass greater than the fabric of the wrap; and a plurality of belts attached to the wrap, wherein a first belt of the plurality of belts attaches to a second belt of the plurality of belts to secure the wrap over the fabric base, and wherein each weighted region is disposed entirely within the wrap.

* * * * *